US012788302B2

(12) United States Patent
Wang et al.

(10) Patent No.: US 12,788,302 B2
(45) Date of Patent: Nov. 10, 2026

(54) SYSTEM FOR COMA EVALUATION

(71) Applicant: SHANXI MEDICAL UNIVERSITY, Taiyuan (CN)

(72) Inventors: Hongxing Wang, Taiyuan (CN); Keming Yun, Taiyuan (CN)

(73) Assignee: SHANXI MEDICAL UNIVERSITY, Taiyuan (CN)

( * ) Notice: Subject to any disclaimer, the term of this patent is extended or adjusted under 35 U.S.C. 154(b) by 207 days.

(21) Appl. No.: 18/650,338

(22) Filed: Apr. 30, 2024

(65) Prior Publication Data

US 2025/0114026 A1    Apr. 10, 2025

(30) Foreign Application Priority Data

Oct. 9, 2023 (CN) ........................ 202311299870.9

(51) Int. Cl.

*A61B 5/377* (2021.01)
*A61B 5/301* (2021.01)
*A61B 5/31* (2021.01)
*A61B 5/398* (2021.01)

(52) U.S. Cl.

CPC .............. *A61B 5/377* (2021.01); *A61B 5/301* (2021.01); *A61B 5/31* (2021.01); *A61B 5/398* (2021.01)

(58) Field of Classification Search

CPC ......... A61B 5/398; A61B 5/301; A61B 5/377; A61B 5/31; A61B 5/4821
USPC .......................................................... 600/301
See application file for complete search history.

(56) References Cited

U.S. PATENT DOCUMENTS 11,696,682 B2 * 7/2023 Tran ......................... A43B 3/42 600/301

FOREIGN PATENT DOCUMENTS

CN 102178514 A * 9/2011 ............... A61B 5/00
CN 107468243 12/2017

OTHER PUBLICATIONS

Birger Johnsen et al. "Common patterns of EEG reactivity in post-anoxic coma identified by quantitative analyses" Clinical Neurophysiology vol. 142, Oct. 2022, pp. 143-153.*

(Continued)

*Primary Examiner* — Igor N Borissov
(74) *Attorney, Agent, or Firm* — Michael Ye; Kalos Athena Wang PLLC

(57) ABSTRACT

A system for coma evaluation is provided, including: a stimulation-generating module operably affixed to a comatose patient for generating controllable stimulation signals to be applied to a target area on the comatose patient; a biosignal collecting module for acquiring a first EEG signal and a first EOG signal of the comatose patient in temporal association with the stimulation signals; and a processing module communicatively coupled to the biosignal collecting module, for separately processing the first EEG signal to obtain a stimulation EEG signal and a composite EOG signal; for processing the composite EOG, according to a second EOG signal measured without application of stimulation signals, to obtain an EOG signal relating to the induced eye-movement response of the comatose patient; and comprehensively processing the induced EOG signal and the stimulation EEG signal, so as to obtain a second EEG signal and evaluate coma severity of the comatose patient.

18 Claims, 2 Drawing Sheets

(56) References Cited

OTHER PUBLICATIONS

R.J. Croft et al. "Removal of ocular artifact from the EEG: a review" R.J. Croft et al. Department of Psychology, University of Wollongong, Australia; 1999, p. 5-19.*

Stefaan Six et al. "Comfort in palliative sedation (Compas): a transdisciplinary mixed method study protocol for linking objective assessments to subjective experiences" BMC Palliative Care; 2018, p. 1-7.*

* cited by examiner

SYSTEM FOR COMA EVALUATION

This application claims priority to Chinese Patent Application No. CN 202311299870.9 filed on Oct. 9, 2023, which is hereby incorporated by reference as if fully set forth herein.

BACKGROUND OF THE APPLICATION

Field

The present disclosure generally relates to the processing of biomedical signals and, more particularly, to a system for coma evaluation.

Description of Related Art

Most patients with cardiac arrest (CA) at the post-resuscitation phase can lapse into a coma after the return of spontaneous circulation (ROSC) due to hypoxic-ischemic brain damage (HIBD), and withdrawal of life-sustaining therapy (WLST) will be considered if the output of neural signals is weak. Therefore, it is important to make a timely and accurate evaluation of the level of consciousness of a patient in a coma so as to prevent early and late WLST. Clinically, the Glasgow Coma Scale is used as a reliable tool to measure the level of consciousness of a patient, and it includes three different scoring systems, namely eye-opening response, verbal response, and motor response. However, evaluation based on this scale is made through observation and is subject to significant deviations due to the subjectivity of medical staff.

CN107468243A discloses a method for evaluating coma severity, which comprises: acquiring EEG data of a patient with coma, pre-processing the EEG data to obtain pure EEG signals, and evaluating coma severity corresponding to the patient according to the pure EEG signals.

Currently, it is difficult to quantify coma severity, and even the least possibility of regaining consciousness can make medical staff and family members of a patient decide to rescue the patient and maintain the life-sustaining therapy for the patient. If the determination is inaccurate and the patient eventually fails to regain consciousness or goes into a longer coma, the consumption of medical resources, economic pressure, and psychological stress undergone by the family of the patient will turn out to be in vain. While the prior disclosure teaches the use of electroencephalography (EEG) analysis for coma evaluation, it fails to provide any solution to quantify variations in the eye-movement signal intensity of a patient during coma. It is known that the eyes are close to the brain. Since physiologically, humans have high eye blinking frequency, artifact signals caused by eye movement always exist in observed EEG signals. These artifact signals can prevent accurate quantitative analysis of EEG signals and, in turn, mislead the decisions of medical staff. Consequently, improper use of medical resources in unpromising rescue may impede timely treatment to patients really worthy of rescuing, or the treatment may put rescued patients at potential risk. In view of this, there is a pressing need for a system or a method that can achieve accurate, quantitative coma analysis for comatose patients to facilitate the estimation of prognosis.

Since there is certainly a discrepancy between the existing art comprehended by the applicant of this patent application and that known by the patent examiners, and since there are many details and disclosures disclosed in literature and patent documents that the applicant has referred during the creation of the present disclosure not exhaustively recited here, it is to be noted that the present disclosure shall include technical features of all of these known works, and the applicant reserves the right to supplement the application with the related art more existing technical features as support according to relevant regulations.

SUMMARY

In view of the shortcomings of the art known by the inventors, the present disclosure provides a system for coma evaluation to address at least one technical issue existing in the art.

To achieve the foregoing objective, the present disclosure provides a system for coma evaluation, which comprises:

- a stimulation generating module, which is operably affixed to a comatose patient and is configured to generate at least one kind of controllable stimulation signals that are to be applied to a target area of the comatose patient;
- a biosignal collecting module, which is configured to acquire the first EEG signal and the first electrooculography (EOG) signal of the comatose patient that is in temporal association with at least one kind of stimulation signal; and
- a processing module, which is communicatively coupled to the biosignal collecting module and is configured to process the first EEG signal according to the first EOG signal to obtain a second EEG signal and evaluate the coma severity of the comatose patient according to the second EEG signal.

Preferably, the processing module processes the first EEG signal according to the first EOG signal to obtain the second EEG signal through:

- performing separation processing on the first EEG signal to obtain a stimulation EEG signal and a composite EOG signal;
- processing the composite EOG signal according to a second EOG signal that is measured without application of the stimulation signals to obtain an EOG signal that relates to the induced eye-movement response of the comatose patient; and
- performing comprehensive processing on the EOG signal relating to the induced eye-movement response and the stimulation EEG signal to obtain the second EEG signal.

Preferably, the processing module evaluates the coma severity of the comatose patient according to the second EEG signal through:

- calculating a difference between the second EEG signal and a resting-state EEG signal of the comatose patient that is measured without application of the stimulation signals to determine a response level of the comatose patient concerning the stimulation signal and evaluating the coma severity of the comatose patient according to the response level.

Preferably, the processing module calculates the difference between the second EEG signal and the resting-state EEG signal to determine the response level of the comatose patient concerning the stimulation signals through:

- performing separation processing on a third EEG signal that is measured without application of the stimulation signals so as to acquire the resting-state EEG signal and an EOG signal that relates to the involuntary eye-movement response of the comatose patient;

calculating a signal-energy difference and/or a corresponding EEG-waveform difference between the second EEG signal and the resting-state EEG signal; and determining the response level of the comatose patient with respect to the stimulation signals according to the signal-energy difference and/or the corresponding EEG waveform difference.

Currently, the Glasgow Coma Scale is used as a reliable tool to measure the coma severity of a patient, and it includes three different scoring systems, namely eye-opening response, verbal response, and motor response. The sum of the evaluated scores of the three systems is the final coma scale. When conducting an evaluation for the foregoing three systems, medical staff simply observe natural responses without adding any stimulation to the observed patients. However, their observation does not consider patients' responses under external stimulation and thus tends to have subjectivity-related deviations. Particularly, eye-movement artifact signals often seen in measured eye-movement signals can cause interference and lead to mis-determination of results, making the evaluation inaccurate and failing to reflect the objective severity. For example, a prior patent document numbered CN107468243A discloses a method and a device for evaluating coma severity; the method therein comprises acquiring EEG data of a patient with coma, pre-processing the EEG data to obtain pure EEG signals, and evaluating coma severity corresponding to the patient according to the pure EEG signals. As described in the prior disclosure, coma evaluation is conventionally achieved using patients' pure EEG signals. The main attempt of the known method is to improve the accuracy of coma evaluation by reducing manual factors that cause interference in the process of coma evaluation, preventing subjectivity of medical staff from deviating from evaluation results, and in turn, minimizing mis-determination. However, to prevent interference from human factors, it is necessary to take additional compensatory means to achieve coma evaluation. For this reason, sample entropy is introduced into coma evaluation. Specifically, sample entropy corresponding to pure EEG signals are calculated, so that coma severity can be evaluated according to the threshold range in which the sample entropy falls, thereby accomplishing quantitative evaluation of coma level and improving evaluation efficiency. In other words, for acquiring pure EEG signals, the known method has to eliminate the use of any additional, artificial stimulation, and this is entirely opposite to the technical scheme of the present disclosure that involves removing eye-movement artifact signals from post-stimulation EEG signals of patients.

EEG signals are very small in amplitude, and for this reason, tend to be interfered by artifacts that are generated when eyes of a patient, which are so close to the brain, have physiologically unavoidable movement, such as blinks and eye movements, during EEG measurement. These eye-movement artifacts often have frequency overlap with the measured EEG signals and form unpreventable, significant noise in EEG signals. In addition to such eye-movement artifacts, there are other biological artifacts, like muscle artifacts, heart artifacts, etc. To overcome the foregoing interfering noises, the present disclosure uses intentionally applied external stimulation to amplify activities of EEG waves of comatose patients, so as to generate beneficial measurement data, which in turn leads to more accurate screening of the expected signals. Further, the present disclosure provides comatose patients with a potential positive impact that may help the comatose patients to regain consciousness with the application of external stimulation and uses the eye-movement response of the comatose patients as a reference for predicting recovery trends of the comatose patients to achieve reflex and proactive adjustment of treatment. To be specific, the present disclosure uses the EEG collecting unit to collect the first EEG signal measured with the stimulation signals and the third EEG signal measured without applying the stimulation signals. Afterward, an existing extraction analysis method (e.g., wavelet transform, independent variable analysis, etc.) is used to process the first EEG signal and the third EEG signal, respectively. Therein, separation processing is performed on the first EEG signal to acquire a stimulation EEG signal and a composite EOG signal, and separation processing is also performed on a third EEG signal measured without application of the stimulation signals so as to acquire a resting-state EEG signal and an EOG signal relating to the involuntary eye-movement response. The first EEG signal and the third EEG signal before processing are composite signals containing plural spectral components. After they are pre-processed and have the technology-inherent artifacts removed, the first EEG signal and the third EEG signal can be processed into biosignals containing the EEG spectral component and the EOG spectral component, respectively, through feature extraction and decomposition.

In the present disclosure, the denoising process for removing eye-movement artifact signals from EEG signals of the patient under stimulation specifically removes EOG signals that relate to spontaneous eye movement caused by patient natural life activities from eye-movement artifact signals and preserves the EOG signals relating to eye movement induced by external stimulation, thereby obtaining composite EEG signals that relate to eye-movement response under stimulation. Afterward, the response level of the patient to external stimulation can be determined according to the numeral difference between the pure pre-stimulation EEG signal (the so-called resting-state EEG signal) and the post-stimulation EEG signal. Then, a quantitative evaluation of the coma severity can be made according to the response level of the patient. Different from the known scheme for filtration of eye-movement artifact signals that removes all EOG components relating to eye movement, the present disclosure instead preserves the EOG components rising from the eye movement of a patient induced by external stimulation so as to achieve the maximal preservation of EOG components relating to the response of the patient to external stimulation, thereby ensuring solid and accurate evaluation of coma according to the response level.

Preferably, the processing module evaluates the coma severity of the comatose patient according to the response level of the comatose patient with respect to the stimulation signals through:

defining an EEG signal-energy threshold range and/or an EEG-waveform threshold range relating to the response level of the comatose patient with respect to the stimulation signals and determining a coma severity corresponding to the EEG signal-energy threshold range and/or the EEG-waveform threshold range as the coma severity of the comatose patient.

Preferably, before processing the first EEG signal according to the first EOG signal to obtain the second EEG signal, the processing module performs the steps:

pre-processing the first electroencephalogram signal so as to remove linear trends, direct-current components and/or power-line interferences therefrom; and filtering the pre-processed first EEG signal.

Preferably, in the present disclosure, the stimulation-generating module generates the at least one kind of controllable stimulation signals through:

- alternately or synchronously applying at least two types of the stimulation signals to the target area of the comatose patient; and/or
- adjusting the at least two kinds of the stimulation signals applied to the target area of the comatose patient in terms of frequency and/or intensity.

Preferably, a system for coma evaluation of the present disclosure may further comprise an image-collecting module for acquiring image information that relates to the eye-movement response of the comatose patient. The processing module is communicatively coupled to the image collecting module in a way that the processing module records the first EOG signal and/or the second EOG signal, which is associated with the image information.

Preferably, in the present disclosure, the stimulation signals may comprise one or more kinds of the following stimulation signals: electric stimulation signals, thermal stimulation signals, and mechanical stimulation signals. Further, if the stimulation signals are electric stimulation signals herein, the target area to which the electric stimulation signals are applied is the median nerve and/or a nerve nucleus in the superior colliculus of the comatose patient.

Preferably, the present disclosure further involves a method for coma evaluation, which comprises the following steps:

- generating at least one kind of controllable stimulation signals to be applied to a target area of a comatose patient;
- acquiring a first EEG signal and a first EOG signal of the comatose patient having temporal association with at least one kind of stimulation signals; and
- processing the first EEG signal according to the first EOG signal so as to obtain a second EEG signal, and evaluating the coma severity of the comatose patient according to the second EEG signal.

DETAILED DESCRIPTION

The following description will be directed to some preferred embodiments as depicted in the accompanying drawings to make the advantages and features of the present disclosure clear to people skilled in the art and to better define the scope of the present disclosure. Although the accompanying drawings depict some exemplary modes of the present disclosure, it is to be understood that the modes referred to herein are only illustrative but not intended to limit the present disclosure.

The present disclosure provides a system for coma evaluation, which may comprise the following three primary parts.

A stimulation generating module 10 is operatable affixed to a comatose patient and is configured to generate at least one kind of controllable stimulation signals that are to be applied to a target area on the comatose patient.

A biosignal collecting module 20 is configured to acquire a first EEG signal and a first EOG signal of the comatose patient that are in temporal association with the at least one kind of stimulation signals. Herein, the term "EEG" refers to electroencephalography, and the term "EOG" refers to electrooculography.

A processing module 30 is communicatively coupled to the biosignal collecting module 20, and is configured to process the first EEG signal according to the first EOG signal so as to obtain a second EEG signal, and evaluate coma severity of the comatose patient according to the second EEG signal.

Figure 1:
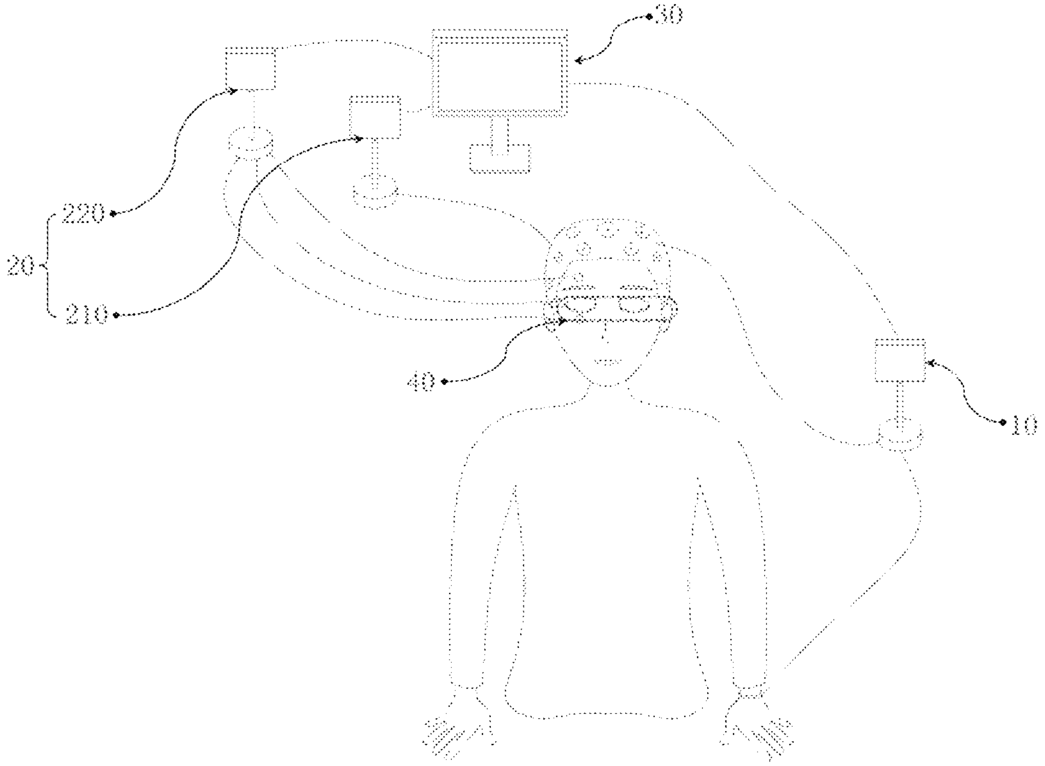
FIG. 1 is a schematic structural drawing showing a system for coma evaluation according to the present disclosure in a preferred embodiment connected to a patient with coma.

FIG. 1, according to the present disclosure, shows a basic hardware structure for the system for coma evaluation to be in connection with a comatose patient. Specifically, as shown in FIG. 1, the disclosed system may generally be composed of three parts, including patient stimulation, data collection, and data analysis. Particularly, the three parts are a stimulation generating module 10 for applying or providing external stimulation to a comatose patient, a biosignal collecting module 20 for acquiring bioelectric signals of the comatose patient before/during/after his/her reception of the external stimulation, and a processing module 30 capable of evaluating the comatose patient for the coma severity or the possibility of regaining consciousness according to these bioelectric signals.

According to one preferred mode, as shown in FIG. 1, the biosignal collecting module 20 may comprise an EEG collecting unit 210 for collecting EEG signals of the comatose patient and an EOG collecting unit 220 for collecting EOG signals of the comatose patient. Further, in the present disclosure, the EEG signals collected by the EEG collecting unit 210 may include a first EEG signal measured with the application of external stimulation and a third EEG signal measured without the application of external stimulation. The EOG signals collected by the EOG collecting unit 220 may include the first EOG signal measured with the application of stimulation and a second EOG signal measured without the application of stimulation.

According to one preferred mode, the EEG collecting unit 210 may be an EEG collecting device, such as an EEG collecting device that comprises one or more EEG collecting electrodes (for which the arrangement can be found in related standards). The EOG collecting unit 220 may be non-intrusive EOG collecting electrodes, such as a pair of EOG collecting electrodes attached to the upper and lower eyelids of the patient, respectively. The EOG collecting electrodes acquire EOG signals by detecting displacement of upper and lower eyelids as a part of the eye-movement response of the patient. Since the collection of EEG and EOG signals is well-known in the art and is not what the inventor wants to improve, the detailed description thereto is omitted for succinctness.

According to one preferred mode, before processing the EEG signals collected by the EEG collecting unit 210 and the EOG signals collected by the EOG collecting unit 220, in response to the reception of those collected signals, the processing module 30 conducts pre-processing to remove technical noises therefrom. For example, to denoise EEG signals, the hardware configuration of the EEG collecting device may comprise a signal amplifier, a filter circuit, and an A/D converter. Specifically, EEG signals are low-frequency, and the signal amplifier may make these low-frequency EEG signals generate very high input impedance. The filter circuit filters the amplified EEG signals for denoising, so as to increase the signal-to-noise ratio of these EEG signals. Then the A/D converter converts the filtered analog EEG signals into digital EEG signals.

Further, when receiving the amplified, filtered EEG signals from the EEG collecting unit 210, the processing module 30 pre-processes the EEG signals to remove linear trends, direct-current components, and power-line interference therefrom. Then, filtration for a predetermined frequency range is conducted. Specifically, the power-line interference (50/60 Hz) primarily comes from the grid. When electrodes have high impedance, power-line interference can be introduced. The power-line interference may be removed using a 50/60 Hz band-stop filter. Filtration may be achieved using a band-pass filter.

According to one preferred mode, external stimulation is applied in the present disclosure for the reasons described below. An EEG signal is a time-variant, unsteady signal with strong noises and subtle electrical activities, so its amplitude is small. EEG signals of comatose patients can be particularly weak, and are more sensitive to technical noises (e.g., inherent noises of measuring and recording devices, environmental noises from external electromagnetic radiation sources, impedance noises caused by poor contact between electrodes and skin, and/or movement artifacts from the cables, etc.) and/or biological artifacts (e.g., eye-movement artifacts, muscle artifacts, etc.). All these make it a challenge to accurately measure EEG signals from comatose patients. Therefore, the introduction of external stimulation is helpful in amplifying EEG wave activities of comatose patients and thus facilitates obtaining beneficial and/or useful measurement data. Secondly, the present disclosure provides comatose patients with a potential positive impact that may help the comatose patients to regain consciousness with the application of external stimulation and uses the eye-movement response of the comatose patients as a reference for predicting recovery trends of the comatose patients so as to achieve reflex and proactive adjustment of treatment.

According to one preferred mode, the stimulation generating module 10 may be one or more of the followings: an electric stimulator, a thermal stimulator, and a mechanical stimulator. Preferably, the present disclosure uses an electric stimulator (e.g., a transcutaneous electrical nerve stimulator) to apply for introduce low-frequency pulses to a target on the skin of the comatose patient so as to stimulate the corresponding nerves. Specifically, when electric stimulation is implemented herein, one or more electric stimulators may be operably affixed to the wrist and/or head of a comatose patient so as to apply stimulative electric pulses to the target nerve of the comatose patient.

According to one preferred mode, when the electric stimulator is affixed to (e.g., in contact with or inserted into) the wrist of the comatose patient, it mainly applies electric pulse stimulation to the median nerve of the comatose patient. For example, electric stimulators (e.g., non-intrusive skin patch electrodes) in a pair are positioned to be aligned with the median nerve at the wrist joint in the lower arm of the comatose patient (approximately at the center of the palmar side of the wrist joints) with a preset distance therebetween. Alternatively, where the electric stimulator is affixed to (e.g., in contact with or inserted into) the head of the comatose patient, it mainly applies electric pulse stimulation to the nerve nucleus at the superior colliculus of the comatose patient. Particularly, since the nucleus of the oculomotor nerve is located at the superior colliculus in the midbrain and is the major motor nerve dominating eye muscles, after stimulation is applied to the nerve nucleus at the superior colliculus, the EOG collecting unit 220 can collect EOG signals generated as a result that the oculomotor nerve at the superior colliculus has eye movement under stimulation.

Optionally, in an example where the stimulation generating module 10 is an electric stimulator, controllable electric pulse stimulation is applied to a target area of the comatose patient through the following procedure. First, a 5 Hz square-wave pulse lasting for 2 seconds is applied to the median nerve at one side (e.g., the left side) of a comatose patient to give two times of electric pulse stimulation, with an interval of 5 minutes. Afterward, at the median nerve of the other side of the comatose patient, two times of electric pulse stimulation are applied with the same intensity and time settings. After electric pulse stimulation to the median nerves is done, the same process is applied to the nerve nucleus at the superior colliculus of the comatose patient with the same intensity and time settings.

It is contemplable that the aforementioned details for the application of electric pulse stimulation to a comatose patient through an electric stimulator (e.g., arrangement of electrodes, the frequency, and/or the cycle) are exemplary and not limiting. In some optional modes, thermal stimulators and mechanical stimulators (e.g., intrusive or non-intrusive pain stimulators) may be used instead for providing a comatose patient with external stimulation. Therein, the exact arrangement (e.g., the layout of the stimulators) and the parameters for stimulation (e.g., the cycle, the intensity, etc.) of the thermal stimulators and mechanical stimulators may be set by a person skilled in the art according to practical needs. For example, an electric stimulator may be dangerous to patients with heart problems in some cases and may interfere with other physiological monitors in the same environment. Moreover, in addition to the foregoing electric stimulator, thermal stimulator, and mechanical stimulator, the stimulation generating module 10 may alternatively be a stimulation device implementing acoustic stimulation or optical stimulation in the form of a stimulation signal that induces physiological reaction (e.g., verbal response, eye-movement response, muscle motor response, etc.) of comatose patients.

EEG signals are small in amplitude, with their frequency ranging between 0.5 and 50 Hz. Besides, eyes are very close to the brain and always have physiologically unavoidable movements, like blinks or other eye movements, during EEG measurement. The movement causes artifacts that are very likely to have frequency overlap with the EEG signal. It is thus arguable that eye-movement artifacts represent an unavoidable, primary interfering noise in an EEG signal. In addition to eye-movement artifacts, there are many other biological artifacts, like muscle artifacts, heart artifacts, etc. In some optional modes, therefore, in addition to the removal of eye-movement artifacts, processing of the EEG signals may further include the removal of muscle artifacts, heart artifacts, etc. Nevertheless, these biological artifacts are usually trivial (e.g., the heart is relatively far from the site for EEG measurement) or contingent (e.g., a muscle artifact mainly happens when muscles at the face or the neck contract for swallowing or occlusion), and thus the present disclosure is focused on removal of eye-movement artifacts. It is contemplable that the biosignal collecting module 20 may further comprise devices for collecting other bioelectric signals. For example, the biosignal collecting module 20 may further comprise an electromyography collecting device, an electrocardiogram collecting device, etc.

Thus far, in order to remove EOG artifacts from an EEG signal, the EEG signal is usually pre-processed for removal of, for example, technology-inherent interfering noises from the EEG signal, and then EOG signals are removed directly using a method like wavelet transform (WT), Hilbert-Huang transform (HHT), independent component analysis (ICA), and canonical correlation analysis (CCA), so as to obtain pure EEG signals. As known, there are three kinds of human eye-movement responses: 1. voluntary eye-movement response; 2. involuntary (spontaneous) eye-movement response; and 3. reflective (induced) eye-movement response. Therein, the voluntary eye-movement response is generated in response to an external instruction as a decision made by the brain through thinking, such as the case where a patient is ordered to open their eyes. The involuntary (spontaneous) eye-movement response is determined by the human normal physiological response (dopaminergic activity), such as the case where a patient blinks spontaneously and unconsciously due to dryness of the conjunctiva and cornea, which are physiologically unavoidable. Reflex (induced) eye-movement response is triggered by sudden, strong stimulation in the form of, for example, electricity, heat, sound, light, or air. Among the different kinds of eye-movement response, in addition to spontaneous, unconscious eye movement, reflex (induced) eye-movement response triggered by strong external stimulation is highly indicative with respect to the coma severity of a comatose patient, and these kinds of reflex (induced) eye-movement response are usually in linear or non-linear positive correlation with additional, reflex stimulation. Therefore, opposite to the known methods in which all EOG signals relating to eye-movement response are removed without exception, the present disclosure conducts the removal of EOG signals in a selective or specific manner. In other words, according to the present disclosure, EOG signals identified as relating to involuntary (spontaneous) eye-movement response are removed, while EOG signals relating to reflex (induced) eye-movement response are preserved, while the EOG signals relating to reflex (induced) eye-movement response and other spectral components of the EEG signals are fit to form EEG data to be used for coma evaluation.

In view of this, according to the present disclosure, the process in which the processing module 30, according to the first EOG signal that is acquired by the EOG collecting unit 220 and is in temporal association with the at least one kind of stimulation signals, processes the first EEG signal acquired by the EEG collecting unit 210 so as to obtain the second EEG signal may comprise the following steps.

First, the processing module 30 performs separation processing on the first EEG signal so as to acquire a stimulation EEG signal and a composite EOG signal.

Then, the processing module 30, according to the second EOG signal measured without applying the stimulation signals, processes the composite EOG signal to acquire the induced EOG signal.

At last, the processing module 30 comprehensively processes the induced EOG signal and the stimulation EEG signal so as to acquire the second EEG signal.

To be specific, the EEG collecting unit 210 collects the first EEG signal measured with the application of the stimulation signals, and the third EEG signal measured without the application of the stimulation signals. With an existing extraction analysis method (such as wavelet transform and independent variable analysis as described previously), the first EEG signal and the third EEG signal are processed, respectively. The first EEG signal and the third EEG signal, before processing, are composite signals containing plural different spectral components. After the preprocessing that removes technology-inherent artifacts, the first EEG signal and the third EEG signal can be processed into biosignals containing EEG spectral components and EOG spectral components by means of feature extraction and decomposition. Specially, with the EEG signal and the EOG signal so obtained, a corresponding spectrogram or waveform can be produced to facilitate extraction or comparison of EEG signal-energy and their distribution characteristics in the time domain and the frequency domain. The frequency or waveform characteristics extracted and analyzed from the spectrogram or the waveform chart can be used subsequently for coma evaluation of the comatose patient.

According to one preferred mode, without the application of external stimulation, EOG signals extracted or separated from the corresponding third EEG signal are mainly caused by the involuntary (spontaneous) eye-movement response of the comatose patient. With the application of external stimulation, EOG signals extracted or separated from the corresponding first EEG signal are mainly caused by involuntary (spontaneous) eye-movement response and reflex (induced) eye-movement response of the comatose patient, and are EOG signals composed of plural different eye-movement spectral components.

Further, the second EOG signal acquired by the EOG collecting unit 220 without the application of external stimulation is used for matching to identify the EOG spectral components split or separated from the third EEG signal through feature extraction or decomposition (e.g., wavelet transform, independent variable analysis, etc.), thereby determining a single EOG signal corresponding to the involuntary (spontaneous) eye-movement response of the comatose patient. Additionally, the first EOG signal acquired by the EOG collecting unit 220 with the application of external stimulation is used for matching to identify the EOG spectral components split or separated from the first EEG signal through feature extraction or decomposition (e.g., wavelet transform, independent variable analysis, etc.), thereby determining composite EOG signals corresponding to involuntary (spontaneous) eye-movement response and reflex (induced) eye-movement response of the comatose patient.

Furthermore, according to the determined single EOG signal corresponding to involuntary (spontaneous) eye-movement response of the comatose patient, a known extraction analysis method (e.g., wavelet transform or independent variable analysis as described previously) is used to process the composite EOG signals corresponding to involuntary (spontaneous) eye-movement response and reflex (induced) eye-movement response of the comatose patient, so as to acquire reflex (induced) EOG signals from the composite EOG signals. Then the processing module 30 comprehensively processes the reflex (induced) EOG signal and the pure EEG signal, split or separated from the first EEG signal and so called as the stimulation EEG signal generated under external stimulation, into the second EEG signal, which can be used as a reference for coma evaluation of the patient coma.

According to one preferred mode, in the present disclosure, the processing module 30 evaluates the coma severity of the comatose patient according to the second EEG signal through the following process. First, the processing module 30 compares the second EEG signal and the resting-state EEG signal measured without application of stimulation (i.e., the EEG spectral components left in the third EEG signal after the single EOG signal relating to involuntary (spontaneous) eye-movement response of the comatose patient is slit or separated) to determine difference therebetween and accordingly determines the response level of the comatose patient with respect to the stimulation signal, and use the response level as the evaluation result for coma severity.

It is contemplable that, in the present disclosure, the first EEG signal is "an EEG signal that is generated when external stimulation is applied to a comatose patient and contains composite EOG components" acquired by the EEG collecting unit 210. The second EEG signal is "an EEG signal that is generated when external stimulation is applied to a comatose patient and only contains induced EOG components" obtained by the processing module 30 through processing. The third EEG signal is "an EEG signal that is generated when there is no external stimulation applied to the comatose patient and contains only involuntary EOG components" acquired by the EEG collecting unit 210. The stimulation EEG signal is an EEG component obtained by removing composite EOG components (i.e., composite EOG signals relating to involuntary eye-movement response and induced eye-movement response) from the first EEG signal. The resting-state EEG signal is an EEG component obtained by removing the single EOG component (i.e., an EOG signal relating to involuntary eye-movement response) from the third EEG signal.

The first EOG signal and the second EOG signal are acquired by the EOG collecting unit 220. Therein, the first EOG signal is an EOG signal that relates to the eye-movement response of the comatose patient when external stimulation is not applied. The second EOG signal is an EOG signal that relates to the eye-movement response of the comatose patient when external stimulation is not applied.

Specifically, after the second EEG signal is acquired, the processing module 30 processes the second EEG signal and the resting-state EEG signal measured without application of stimulation into corresponding first and second EEG charts, respectively, and extracts waveform characteristics of the first EEG chart and the second EEG chart. Further, the processing module 30 compares waveform characteristics of the first EEG chart and the second EEG chart, and uses the waveform difference therebetween as the analytic result of how the comatose patient responds to external stimulation. To be specific, the waveform characteristics usually include the frequency, amplitude, etc., of wave bands in the EEGs. A large waveform difference usually relates to a patient exhibiting strong response, which means that the patient is very likely to recover and is therefore worth rescuing. On the contrary, a small waveform difference usually relates to a patient exhibiting a weak response, which means that the patient is unlikely to recover and faces a poor prognosis, so it may be time to determine the timing for WLST.

Preferably, processing module 30 comparatively analyzes the distribution characteristics of the second EEG signal and the resting-state EEG signal measured without the application of stimulation for the distribution of signal energy in the time domain and the frequency domain. Then, it combines the result of the comparison between the second EEG signal and the resting-state EEG signal in terms of signal energy with the result of comparing the waveform characteristics and uses the combination as the analytic result of response capability in terms of the external stimulation. In some optional modes, evaluating the coma severity of a patient using the collected EEG signal may further be achieved by means of a machine learning model that is pre-trained using data from a large number of EEG samples.

Specially, EEG-waveform threshold ranges or EEG signal-energy threshold ranges may be defined for different coma levels. By calculating the waveform difference between the first EEG chart and the second EEG chart, and/or the signal-energy difference between the second EEG signal and the resting-state EEG signal, and comparing the calculated waveform difference and signal-energy difference with EEG-waveform difference threshold ranges and/or EEG signal-energy difference threshold ranges corresponding to different coma levels, the coma severity of the patient can be determined.

Coma is a kind of complete loss of consciousness and is recognized as a critical illness clinically. The present disclosure uses EEG signals of a patient-generated with the application of external stimulation to the patient and containing induced eye-movement signals as a basis to evaluate the response capability of the comatose patient to external stimulation and evaluates coma severity of the patient according to the response capability, thereby achieving more accurate and more efficient evaluation of coma severity.

According to one preferred mode, another objective of the system for coma evaluation of the present disclosure is to: by alternately or synchronously applying different kinds of stimulation signals, and adjusting one or more kinds of stimulation signals in terms of intensity and time, recognize stimulation programs that can bring about obvious reflex (induced) eye-movement response of the patient. These stimulation programs may act as a reference for medical staff to conduct coma evaluation for the patient and can be used as a recommended means for facilitating recovery of the comatose patient. For example, at least two kinds of stimulation signals may be alternately or synchronously applied to the target area of the comatose patient, or one or more kinds of stimulation signals are intermittently or continuously applied to the target area of the comatose patient. Furthermore, adjustments may also be made to one or more kinds of stimulation signals to be applied to the target area of the comatose patient so as to change the frequency or the intensity of the stimulation signals.

Specifically, applying one or more kinds of stimulation signals to the patient alternately may comprise: applying electric stimulation for a first predetermined duration, and then applying mechanical stimulation for a second predetermined duration; or, alternatively, applying mechanical stimulation for the first predetermined duration (or the second predetermined duration), and then applying electric stimulation for the second predetermined duration (or the first predetermined duration). Applying plural different stimulation signals to the patient simultaneously may comprise: simultaneously applying electric stimulation and mechanical stimulation to the patient at a first-time point. Therein, electric stimulation and mechanical stimulation may last for the same or different predetermined stimulation time lengths. For example, electric stimulation lasts to a second-time point and mechanical stimulation lasts to a third-time point. Thus, for patients with coma for different causes (e.g., cerebrovascular injuries, intoxication, concussion, etc.), combinations of different stimulation programs may be used. The processing module 30 may analyze EEG signals corresponding to different stimulation programs (e.g., single-signal stimulation or combined-signal stimulation), and consider the corresponding EOG signal that relates to reflex (induced) eye-movement response, so as to determine a current stimulation program that most suitable for the comatose patient. Parameter setting of these stimulation programs and the EEG signal value of the corresponding patients may be stored in the database of the system in a way that they are associated with each other, and may be used for training and testing a machine learning model, thereby enabling a machine diagnosis model for evaluating coma severity for patients.

Additionally, the present application further discloses an approach for the application of one or more kinds of controllable stimulation signals to a comatose patient over one or more biorhythmic time periods. According to the eye-movement response of the patient to different stimulation programs, the probability of causation between the current stimulation program and consciousness recovery can be determined and used as a reference that directs a second choice of the current stimulation program and the corresponding biorhythmic time period. The biorhythmic time period may, for example, be the dawn, the noon, or the dusk (or before dawn) in a day. The human nervous system usually has its sensitivity changing over different biorhythmic time periods and thus performs differently (e.g., having different forms of eye-movement response) in response to external stimulation. Therefore, applying one or more kinds of controllable stimulation signals to a comatose patient in different biorhythmic time periods may provide valuable data for ascertaining the trend of the patient toward consciousness.

According to one preferred mode, at least one kind of stimulation signal is applied to the patient in at least one first biorhythmic time period (e.g., at dawn), and variations of EEG signal characteristics (e.g., the frequency, the amplitude, etc.) in several first biorhythmic time periods are analyzed. For example, an average fluctuation value of the first EEG signal over several first biorhythmic time periods may be obtained through analysis. Additionally, in at least one second biorhythmic time period (e.g., at dusk), at least one kind of stimulation signal is applied to the patient, and variations in characteristics (e.g., the frequency, the amplitude, etc.) of the EEG signal in several second biorhythmic time periods are analyzed. For example, an average fluctuation value of the second EEG signal over several second biorhythmic time periods may be obtained through analysis. By analyzing and comparing the fluctuation trend of the EEG signals in different biorhythmic time periods (e.g., at dawn or at dusk), information can be obtained and used in determining the possibility that the patient regains consciousness or in identifying the stimulation programs that better facilitate recovery of the patient and the corresponding biorhythmic time periods. For example, by analyzing and comparing the differences between or non-linear variations of the average fluctuation value of the first EEG signal and the average fluctuation value of the second EEG signal, trends of variations of the EEG signals of the patient in different stimulation time periods for different stimulation programs can be learned.

According to one preferred mode, in the present disclosure, the application of stimulation to the comatose patient may be performed using alternative stimulation behavior models (e.g., alternately using or combining different kinds of stimulation signals and adjusting parameters, such as the intensity and the frequency, of the one or more kinds of stimulation signals), so that different levels of response of the patient to these models can be observed. Particularly, the response of the comatose patient relating to induced eye movement under different stimulation behavior models is observed to determine the stimulation behavior model that better facilitates the evaluation of coma. Meanwhile, since the recovery of a comatose patient has a strong correlation with his/her induced eye movement, the selected stimulation behavior model is not only useful for subsequent evaluation of coma severity but also provides prognostic information about the recovery of the patient according to the trend of levels of response relating to induced eye-movement. Besides, as it is expected that the patient will respond better to the selected stimulation behavior model level, the model is not only useful for subsequent evaluation of coma but also believed to be helpful, to some extent, to the comatose patient for regaining consciousness.

Figure 2:
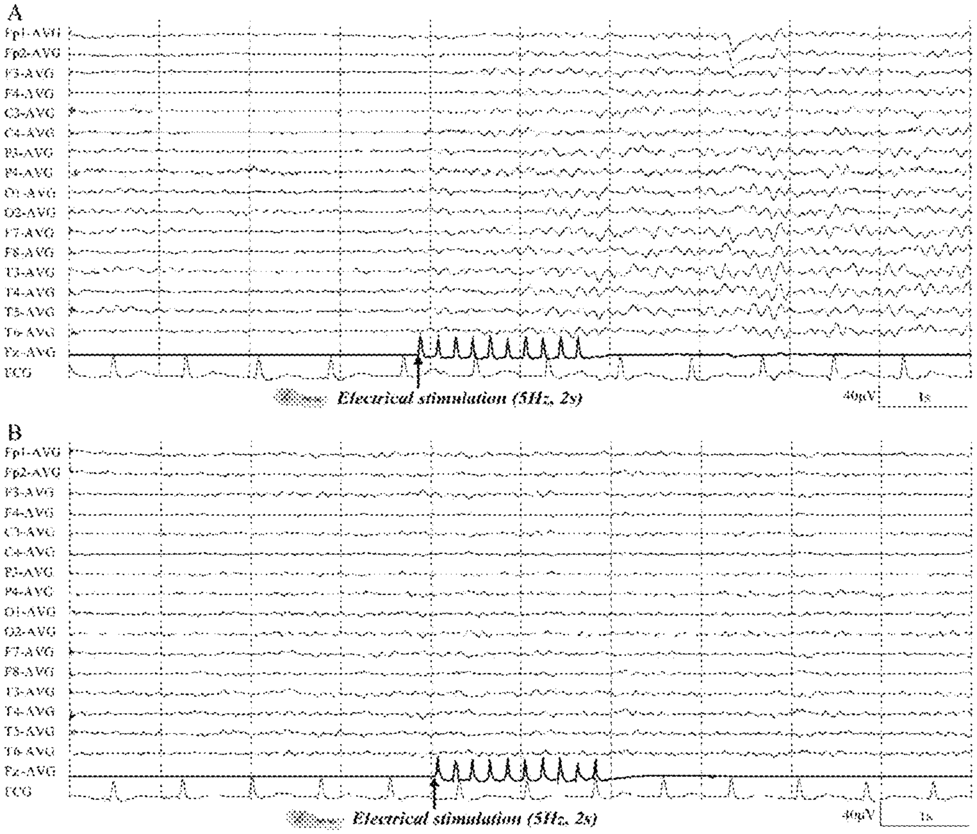
FIG. 2 are EEGs of two patients measured under electric stimulation.

According to one preferred mode, FIG. 2 shows EEGs of two patients under electric stimulation. Therein, FIG. 2A is the EEG of a 40-year-old patient with Cerebral Performance Category (CPC) scored 1. As shown, the EEG signal responded more strongly to electric stimulation. FIG. 2B is the EEG of a 50-year-old non-reflex patient with a CPC score of 4. As shown, the EEG signal had no obvious response to the applied electric stimulation.

According to one preferred mode, as shown in FIG. 1, the system for coma evaluation of the present disclosure may further comprise an image-collecting module 40 communicatively coupled to the processing module 30. The image collecting module 40 may be constructed as an eye cover to be affixed to the eyes of the patient. Specifically, the image collecting module 40 is configured to acquire image information relating to the eye-movement response of the comatose patient, so that the processing module 30 can store the first EOG signal and/or the second EOG signal acquired by the EOG collecting unit 220 and the eye-movement image acquired by the image collecting module 40 into the database in a way that the signal and the image are associated with each other. Further, by combining the eye-movement image and the second EEG signal containing the induced EOG signal, the processing module 30 can compare the eye-movement image and the second EEG signal containing the induced EOG signal with the resting-state eye-movement image and the resting-state EEG signal measured without application of external stimulation, respectively, thereby obtaining the numerical differences that can be used to evaluate the coma severity of the patient.

In some optional modes, the system for coma evaluation of the present disclosure may further comprise input or output devices not shown in the drawings, such as a loudspeaker, a beacon, and/or a microphone. Specifically, the loudspeaker and the beacon can provide the comatose patient with acoustic stimulation and optical stimulation, respectively. The microphone may be used to record the verbal response made by the comatose patient to the external stimulation (e.g., electric stimulation, thermal stimulation, and mechanical stimulation). Thereby, the processing module 30 can use the second EEG signal and the eye-movement image of the comatose patient together with the verbal response to comprehensively assess the coma severity of the patient.

According to one preferred mode, the present disclosure further provides a method for coma evaluation, which may use the disclosed system for coma evaluation as described previously. The method for coma evaluation may comprise the following steps:

- generating at least one kind of controllable stimulation signal to be applied to the target area of the comatose patient;
- acquiring a first EEG signal and a first EOG signal of the comatose patient that are in temporal association with at least one kind of stimulation signals and
- according to the first EOG signal, processing the first EEG signal so as to obtain the second EEG signal, and, according to the second EEG signal, evaluating the coma severity of the comatose patient.

According to one preferred mode, in the present disclosure, processing the first EEG signal according to the first EOG signal so as to obtain the second EEG signal may comprise:

performing separation processing on the first EEG signal so as to acquire a stimulation EEG signal and a composite EOG signal;

according to the second EOG signal generated without application of the stimulation signals, processing the composite EOG signal so as to acquire EOG signals relating to induced eye-movement response; and comprehensively processing EOG signals relating to induced eye-movement response and the stimulation EEG signal so as to acquire the second EEG signal.

According to one preferred mode, in the present disclosure, evaluating the coma severity of the comatose patient according to the second EEG signal may comprise:

calculating a difference between the second EEG signal and a resting-state EEG signal of the comatose patient that is measured without application of the stimulation signals so as to determine a response level of the comatose patient with respect to the stimulation signal and evaluating the coma severity of the comatose patient according to the response level.

According to one preferred mode, in the present disclosure, calculating the difference between the second EEG signal of the comatose patient and the resting-state EEG signal measured without application of the stimulation signals so as to determine the response level of the comatose patient with respect to the stimulation signals may comprise:

performing separation processing on a third EEG signal measured without application of the stimulation signals so as to acquire the resting-state EEG signal and EOG signals relating to involuntary eye-movement response;

acquiring a signal-energy difference between the second EEG signal and the resting-state EEG signal and/or a waveform difference between the corresponding EEGs; and according to the signal-energy difference and/or the waveform difference between the corresponding EEGs, the response level of the comatose patient with respect to the stimulation signals is determined.

According to one preferred mode, in the present disclosure, evaluating the coma severity of the comatose patient according to the response level of the comatose patient with respect to the stimulation signals comprises the following steps:

determining an EEG signal-energy threshold range and/or an EEG-waveform threshold range that relates to the response level of the comatose patient with respect to the stimulation signals; and determining the coma severity corresponding to the EEG signal-energy threshold range and/or the EEG-waveform threshold range as the coma severity of the comatose patient.

According to one preferred mode, in the present disclosure, generating at least one kind of controllable stimulation signal to be applied to the target area of the comatose patient may comprise the following steps:

alternately or synchronously applying at least two kinds of stimulation signals to the target area of the comatose patient; and/or adjusting at least two kinds of stimulation signals applied to the target area of the comatose patient in terms of frequency and/or intensity.

Alternatively, applying at least one kind of controllable stimulation signals to the target area of the comatose patient may be achieved through:

intermittently or continuously applying one or more kinds of stimulation signals to the target area of the comatose patient; and/or adjusting the one or more kinds of stimulation signals applied to the target area of the comatose patient in terms of intensity.

Those skilled in the art should understand that other steps or operations may be included before or after each of the abovementioned steps or between the steps, such as for further optimization and/or improvement of the disclosed method, provided that the purpose of the present disclosure can still be achieved. In addition, although the method of the present disclosure is shown and described as a series of actions performed in sequence, it should be understood that the method is not limited to the sequence. For example, some actions may occur in a different order than described herein. Alternatively, one action can occur simultaneously with another action.

It is to be noted that the particular embodiments described previously are exemplary. People skilled in the art, with inspiration from the disclosure of the present disclosure, would be able to devise various solutions, and all these solutions shall be regarded as a part of the disclosure and protected by the present disclosure. Further, people skilled in the art would appreciate that the descriptions and accompanying drawings provided herein are illustrative and form no limitation to any of the appended claims. The scope of the present disclosure is defined by the appended claims and equivalents thereof. The disclosure provided herein contains various inventive concepts, such as those described in sections led by terms or phrases like “preferably”, “according to one preferred mode,” or “optionally”. Each of the inventive concepts represents an independent conception and the applicant reserves the right to file one or more divisional applications therefor.

What is claimed is:

1. A system for coma evaluation, comprising:

a stimulation generating module, which is operably affixed to a comatose patient and is configured to generate at least one kind of controllable stimulation signal that is to be applied to a target area of the comatose patient, wherein the stimulation generating module comprises an electric stimulator, a thermal stimulator and/or a mechanical stimulator;

a biosignal collecting module, which is configured to acquire the first EEG signal and a first EOG signal of the comatose patient that are in temporal association with at least one kind of stimulation signals, wherein the biosignal collecting module comprises an EEG collecting device; and a processing module, which is communicatively coupled to the biosignal collecting module and is configured to process the first EEG signal according to the first EOG signal so as to obtain a second EEG signal and evaluate the coma severity of the comatose patient according to the second EEG signal;

wherein the processing module processes the first EEG signal according to the first EOG signal so as to obtain the second EEG signal through:

performing separation processing on the first EEG signal so as to obtain a stimulation EEG signal and a composite EOG signal;

processing the composite EOG signal according to a second EOG signal that is measured without application of the stimulation signals so as to obtain an EOG signal that relates to the induced eye-movement response of the comatose patient; and performing processing on the EOG signal relating to the induced eye-movement response and the stimulation EEG signal so as to obtain the second EEG signal.

2. The system of claim 1, wherein the processing module evaluates the coma severity of the comatose patient according to the second EEG signal through:

calculating a difference between the second EEG signal and a resting-state EEG signal of the comatose patient that is measured without application of the stimulation signals so as to determine a response level of the comatose patient with respect to the stimulation signal and evaluating the coma severity of the comatose patient according to the response level.

3. The system of claim 2, wherein the processing module calculates the difference between the second EEG signal and the resting-state EEG signal so as to determine the response level of the comatose patient with respect to the stimulation signals through:

performing separation processing on a third EEG signal that is measured without application of the stimulation signals so as to acquire the resting-state EEG signal and an EOG signal that relates to the involuntary eye-movement response of the comatose patient;

calculating a signal-energy difference and/or a corresponding EEG-waveform difference between the second EEG signal and the resting-state EEG signal; and determining the response level of the comatose patient with respect to the stimulation signals according to the signal-energy difference and/or the corresponding EEG waveform difference.

4. The system of claim 3, wherein the processing module evaluates the coma severity of the comatose patient according to the response level of the comatose patient with respect to the stimulation signals through:

defining an EEG signal-energy threshold range and/or an EEG-waveform threshold range relating to the response level of the comatose patient with respect to the stimulation signals; and determining a coma severity corresponding to the EEG signal-energy threshold range and/or the EEG-waveform threshold range as the coma severity of the comatose patient.

5. The system of claim 4, wherein before processing the first EEG signal according to the first EOG signal so as to obtain the second EEG signal, the processing module performs the steps of:

pre-processing the first EEG signal so as to remove linear trends, direct-current components and/or power-line interferences therefrom; and filtering the pre-processed first EEG signal.

6. The system of claim 5, wherein the stimulation generating module generates at least one kind of controllable stimulation signal through:

alternately or synchronously applying at least two kinds of stimulation signals to the target area of the comatose patient; and/or adjusting the at least two kinds of stimulation signals applied to the target area of the comatose patient in terms of frequency and/or intensity.

7. The system of claim 6, further comprising an image collecting module for acquiring image information that relates to the eye-movement response of the comatose patient, so that the processing module is communicatively coupled to the image collecting module in a way that the processing module such records the first EOG signal and/or the second EOG signal that the first EOG signal and/or the second EOG signal are associated to the image information.

8. The system of claim 7, wherein the stimulation signals include one or more of the followings: an electric stimulation signal, a thermal stimulation signal, and a mechanical stimulation signal.

9. The system of claim 8, wherein the stimulation signals are electric stimulation signals, and the target area for the electric stimulation signals to apply is the nerve nucleus in the median nerve and/or the superior colliculus of the comatose patient.

10. A method for coma evaluation, comprising:

providing a stimulation generating module, which is operably affixed to a comatose patient and is configured to generate at least one kind of controllable stimulation signal that is to be applied to a target area of the comatose patient, wherein the stimulation generating module comprises an electric stimulator, a thermal stimulator and/or a mechanical stimulator;

providing a biosignal collecting module, which is configured to acquire the first EEG signal and the first EOG signal of the comatose patient that are in temporal association with at least one kind of stimulation signals, wherein the biosignal collecting module comprises an EEG collecting device; and providing a processing module, which is communicatively coupled to the biosignal collecting module and is configured to process the first EEG signal according to the first EOG signal so as to obtain a second EEG signal and evaluate the coma severity of the comatose patient according to the second EEG signal;

wherein the processing module processes the first EEG signal according to the first EOG signal so as to obtain the second EEG signal through:

performing separation processing on the first EEG signal so as to obtain a stimulation EEG signal and a composite EOG signal;

processing the composite EOG signal according to a second EOG signal that is measured without application of the stimulation signals so as to obtain an EOG signal that relates to the induced eye-movement response of the comatose patient; and performing processing on the EOG signal relating to the induced eye-movement response and the stimulation EEG signal so as to obtain the second EEG signal.

11. The method of claim 10, wherein the processing module evaluates the coma severity of the comatose patient according to the second EEG signal through:

calculating a difference between the second EEG signal and a resting-state EEG signal of the comatose patient that is measured without application of the stimulation signals so as to determine a response level of the comatose patient with respect to the stimulation signal and evaluating the coma severity of the comatose patient according to the response level.

12. The method of claim 11, wherein the processing module calculates the difference between the second EEG signal and the resting-state EEG signal so as to determine the response level of the comatose patient with respect to the stimulation signals through:

performing separation processing on a third EEG signal that is measured without application of the stimulation signals so as to acquire the resting-state EEG signal and an EOG signal that relates to the involuntary eye-movement response of the comatose patient;

calculating a signal-energy difference and/or a corresponding EEG-waveform difference between the second EEG signal and the resting-state EEG signal; and determining the response level of the comatose patient with respect to the stimulation signals according to the signal-energy difference and/or the corresponding EEG waveform difference.

13. The method of claim 12, wherein the processing module evaluates the coma severity of the comatose patient according to the response level of the comatose patient with respect to the stimulation signals through:

defining an EEG signal-energy threshold range and/or an EEG-waveform threshold range relating to the response level of the comatose patient with respect to the stimulation signals and determining a coma severity corresponding to the EEG signal-energy threshold range and/or the EEG-waveform threshold range as the coma severity of the comatose patient.

14. The method of claim 13, wherein before processing the first EEG signal according to the first EOG signal so as to obtain the second EEG signal, the processing module performs the steps of:

pre-processing the first EEG signal so as to remove linear trends, direct-current components and/or power-line interferences therefrom; and filtering the pre-processed first EEG signal.

15. The method of claim 14, wherein the stimulation generating module generates at least one kind of controllable stimulation signal through:

alternately or synchronously applying at least two kinds of the stimulation signals to the target area of the comatose patient; and/or adjusting the at least two kinds of the stimulation signals applied to the target area of the comatose patient in terms of frequency and/or intensity.

16. The method of claim 15, further comprising an image collecting module for acquiring image information that relates to the eye-movement response of the comatose patient, so that the processing module is communicatively coupled to the image collecting module in a way that the processing module such records the first EOG signal and/or the second EOG signal that the first EOG signal and/or the second EOG signal are associated to the image information.

17. The method of claim 16, wherein the stimulation signals include one or more of the following: an electric stimulation signal, a thermal stimulation signal, and a mechanical stimulation signal.

18. The method of claim 17, wherein the stimulation signals are electric stimulation signals, and the target area for the electric stimulation signals to apply is the nerve nucleus in the median nerve and/or the superior colliculus of the comatose patient.

* * * * *